United States Patent
Ford (10) Patent No.: US 11,257,137 B2
(45) Date of Patent: Feb. 22, 2022

(54) CUSTOMIZED SKIN CARE

(71) Applicant: L Ford, Inc., Corona Del Mar, CA (US)

(72) Inventor: Laleh Ford, Corona Del Mar, CA (US)

(73) Assignee: L FORD, INC., Corona Del Mar, CA (US)

( * ) Notice: Subject to any disclaimer, the term of this patent is extended or adjusted under 35 U.S.C. 154(b) by 214 days.

(21) Appl. No.: 16/373,220

(22) Filed: Apr. 2, 2019

(65) Prior Publication Data

US 2019/0303991 A1 Oct. 3, 2019

Related U.S. Application Data

(60) Provisional application No. 62/651,896, filed on Apr. 3, 2018.

(51) Int. Cl.

| | |
|---|---|
| A61K 36/00 | (2006.01) |
| G06Q 30/06 | (2012.01) |
| A61K 8/73 | (2006.01) |
| A61Q 19/00 | (2006.01) |
| A61K 8/9789 | (2017.01) |
| A61K 8/9728 | (2017.01) |
| A61K 8/35 | (2006.01) |
| A61K 8/34 | (2006.01) |
| A61K 8/60 | (2006.01) |
| A61K 8/49 | (2006.01) |
| A61K 8/64 | (2006.01) |
| A61K 8/368 | (2006.01) |
| A61K 8/365 | (2006.01) |
| A61K 8/92 | (2006.01) |
| A61K 8/19 | (2006.01) |
| A61K 8/41 | (2006.01) |
| A61K 8/9706 | (2017.01) |

(52) U.S. Cl.
CPC .......... *G06Q 30/0621* (2013.01); *A61K 8/19* (2013.01); *A61K 8/345* (2013.01); *A61K 8/347* (2013.01); *A61K 8/355* (2013.01); *A61K 8/365* (2013.01); *A61K 8/368* (2013.01); *A61K 8/41* (2013.01); *A61K 8/498* (2013.01); *A61K 8/4926* (2013.01); *A61K 8/4973* (2013.01); *A61K 8/602* (2013.01); *A61K 8/64* (2013.01); *A61K 8/735* (2013.01); *A61K 8/922* (2013.01); *A61K 8/9706* (2017.08); *A61K 8/9728* (2017.08); *A61K 8/9789* (2017.08); *A61Q 19/007* (2013.01); *A61Q 19/008* (2013.01)

(58) Field of Classification Search
CPC .................................................. G06Q 30/0621
See application file for complete search history.

(56) References Cited

U.S. PATENT DOCUMENTS

| | | | |
|---|---|---|---|
| 6,177,093 B1 * | 1/2001 | Lombardi | A61K 8/00 |
| | | | 424/401 |
| 6,516,245 B1 * | 2/2003 | Dirksing | A45D 40/00 |
| | | | 700/233 |
| 9,060,949 B2 * | 6/2015 | Vielhaber | A61Q 5/00 |
| 2002/0082745 A1 * | 6/2002 | Wilmott | A61K 8/73 |
| | | | 700/233 |
| 2016/0331308 A1 * | 11/2016 | Zhou | A61B 5/0022 |

OTHER PUBLICATIONS

Making Cosmetics, "ActiCaps® Argireline," Dec. 18, 2017, 2 pages [online], [retrieved on Jun. 26, 2019], Retrieved from the Internet: <URL:https://www.makingcosmetics.com/ActiCaps%C2%AE-Argireline_p_1098.html>.
Medisca, "Product No. 7371," Jan. 5, 2018, 2 pages.
Medisca, "Product No. 8961," Dec. 18, 2017, 1 page.

* cited by examiner

*Primary Examiner* — Qiuwen Mi
(74) *Attorney, Agent, or Firm* — Klein, O'Neill & Singh, LLP (57) ABSTRACT

A system for producing a customized skin care product in less than five minutes includes active ingredient premixes, premix dispensers respectively operable to dispense a predefined quantity of the active ingredient premixes by a single dispenser operation, skin care product bases, product base dispensers respectively operable to dispense a predefined quantity of the skin care product bases by a single dispenser operation, and instructions executable by a processor to receive data indicative of a customer's skin condition and generate a recipe for producing a customized skin care product containing specified percentages by weight of two or more active ingredients suited for the customer's skin condition. The recipe defines a number of operations of one or more of the premix dispensers and one of the product base dispensers. The system further includes a mixing machine operable to mix the contents of a closed container filled in accordance with the recipe.

17 Claims, 5 Drawing Sheets

Questionnaire 50

Which of these describes your skin type?
☐ ~~~~~~  ☐ ~~~~~~
☐ ~~~~~~  ☐ ~~~~~~

What would you like to achieve?
☐ ~~~~~~  ☐ ~~~~~~
☐ ~~~~~~  ☐ ~~~~~~

Do you prefer a cream, lotion, or gel?
☐ ~~~~~  ☐ ~~~~~  ☐ ~~~~~

Additional preferences (Scents, etc.)
☐ ~~~~~~  ☐ ~~~~~~
☐ ~~~~~~  ☐ ~~~~~~

FIG. 4

Components:
- Product base A
- Premix D
- Premix E

Container:
- Size 3 (30mL) white

Directions:
1. Dispense ⑥ pumps of Product base A into container
2. Dispense ② pumps of Premix D into container
3. Dispense ① pump of Premix E into container

CUSTOMIZED SKIN CARE

CROSS-REFERENCE TO RELATED APPLICATIONS

The present application claims the benefit of Provisional Application Ser. No. 62/651,896, filed on Apr. 3, 2018, the entire contents of which are expressly incorporated herein by reference.

STATEMENT RE: FEDERALLY SPONSORED RESEARCH/DEVELOPMENT

Not Applicable

BACKGROUND

While off-the-shelf skin care products come in many varieties, the different skin care needs and skin types of individuals makes it difficult to find a perfectly suited skin care product, especially if the individual has multiple concerns such as blemish-prone skin and hyperpigmentation. The difficulty is even greater if the individual also has preferences as to the product's form, fragrance, etc. or has allergies to preservatives.

BRIEF SUMMARY

The present disclosure contemplates various systems and methods for producing a customized skin care product. Active ingredient premixes are prepared in advance, e.g. in a laboratory setting, each premix suited to treat a different skin condition such as hyperpigmentation, acne-prone skin, or wrinkles. Since the active ingredients of a given premix may have different specified final product weight percentages, the relative quantities of each active ingredient in the premix are controlled so that the premix as a whole maintains a single final product weight percentage. When a customer wants to purchase a customized skin care product in a retail setting, the customer fills out a questionnaire indicating his/her skin condition, skin type (e.g. oily, dry, or oily/dry), and preferences with respect to product form (e.g. cream, lotion, gel, or serum), fragrance, etc. A computer program receives the questionnaire data and generates a recipe for producing the customized skin care product. Since the premixes obviate the need for measuring individual active ingredients, the recipe need only define a combination of a specified premix(es), a product base (e.g. cream, lotion, gel, or serum), and any additional components such as fragrances. Since the computer program is provided with data of the dispensers used for each component, where a single dispenser operation (e.g. a single pump) dispenses a predefined quantity, the recipe simply defines a number of dispenser operations for each component. A retail employee can therefore easily fill a container according to the recipe without having to make any measurements, and the contents of the container will have the correct final product weight percentages of each of the active ingredients. The filled container can then be closed, mixed by a mixing machine, and provided to the customer. The entire process from receiving the completed questionnaire to providing the finished product to the customer may take less than fifteen minutes, preferably less than ten minutes, more preferably less than 5 minutes. Thus, unlike conventional custom skin care products that must be ordered in advance, the disclosed systems and methods can satisfy an immediate need for skin care.

In accordance with one embodiment, there is a system for producing a customized skin care product containing specified percentages by weight of two or more active ingredients suited for a customer's skin condition. The system includes a first active ingredient premix including a first combination of active ingredients for treatment of skin, a first premix dispenser operable to dispense a predefined quantity of the first active ingredient premix by a single operation of the first premix dispenser, a second active ingredient premix including a second combination of active ingredients for treatment of skin that is different from the first combination of active ingredients, a second premix dispenser operable to dispense a predefined quantity of the second active ingredient premix by a single operation of the second premix dispenser, a first skin care product base having a form selected from the group consisting of cream, lotion, gel, and serum, a first product base dispenser operable to dispense a predefined quantity of the first skin care product base by a single operation of the first product base dispenser, a second skin care product base having a form selected from the group consisting of cream, lotion, gel, and serum, and a second product base dispenser operable to dispense a predefined quantity of the second skin care product base by a single operation of the second product base dispenser. The second skin care product base is adapted for treatment of a different type of skin than the first skin care product base and/or the form of the second skin care product base is different from the form of the first skin care product base. The system further includes a non-transitory computer readable medium storing instructions executable by a processor to receive data indicative of a customer's skin condition and generate a recipe for producing a customized skin care product containing specified percentages by weight of two or more active ingredients suited for the customer's skin condition, the recipe defining a number of operations of the first premix dispenser and/or a number of operations of the second premix dispenser and further defining a number of operations of the first product base dispenser or the second product base dispenser. The system further includes a mixing machine operable to mix the contents of a closed container filled in accordance with the recipe.

The first skin care product base may be adapted for treatment of a type of skin selected from the group consisting of oily skin, dry skin, and combined oily and dry skin. The second skin care product base may be adapted for treatment of a different type of skin than the first skin care product base selected from the group consisting of oily skin, dry skin, and combined oily dry skin.

The first combination of active ingredients may include two or more items selected from the group consisting of *Glycyrrhiza glabra* extract; *Bellis perennis* flower extract; kojic acid; hydroquinone; resveratrol; a peptide having the International Nomenclature of Cosmetic Ingredients (INCI) name Acetyl Glycyl Beta-Alanine; arbutin; and L-ascorbic acid.

The first combination of active ingredients may include *Glycyrrhiza glabra* extract; *Bellis perennis* flower extract; kojic acid and/or hydroquinone; resveratrol; a peptide having the International Nomenclature of Cosmetic Ingredients (INCI) name Acetyl Glycyl Beta-Alanine; arbutin; and L-ascorbic acid.

The first combination of active ingredients may include two or more items selected from the group consisting of niacinamide; salicylic acid; glycolic acid; lactic acid; argan oil or apricot kernel oil; a sediment having the International Nomenclature of Cosmetic Ingredients (INCI) name Silt; charcoal; and *Aloe barbadensis* concentrate.

The first combination of active ingredients may include niacinamide; salicylic acid; glycolic acid; argan oil or apricot kernel oil; a sediment having the International Nomenclature of Cosmetic Ingredients (INCI) name Silt; charcoal; and *Aloe barbadensis* concentrate.

The first combination of active ingredients may include two or more items selected from the group consisting of a flavonoid complex including purified water having the International Nomenclature of Cosmetic Ingredients (INCI) name Water (Aqua), butylene glycol, *Ginkgo biloba* leaf extract, phenoxyethanol, and ethylhexylglycerin; green tea extract; vitamin E; dimethylaminoethanol (DMAE); Coenzyme $Q_{10}$; plant stem cell; and L-ascorbyl palmitate.

The first combination of active ingredients may include a flavonoid complex including purified water having the International Nomenclature of Cosmetic Ingredients (INCI) name Water (Aqua), butylene glycol, *Ginkgo biloba* leaf extract, phenoxyethanol, and ethylhexylglycerin; green tea extract; vitamin E; dimethylaminoethanol (DMAE); Coenzyme $Q_{10}$; plant stem cell; and L-ascorbyl palmitate.

The first combination of active ingredients may include two or more items selected from the group consisting of a complex of vegetable glycerin having the International Nomenclature of Cosmetic Ingredients (INCI) name Glycerin, purified water having the INCI name Water (Aqua), a chemical having the INCI name Methylglucoside Phosphate, and a chemical having the INCI name Copper Lysinate/Prolinate; a complex having the INCI name *Lactococcus* Ferment Lysate; acetyl hexapeptide-3; palmitoyl tripeptide; algae extract; dipalmitoyl hydroxyproline; Vitamin E Tocopherol retinol; retinyl palmitate; hyaluronic acid; and a chemical having the INCI name Propanediol (and) *Orobanche rapum* Extract.

The first combination of active ingredients may include a complex of vegetable glycerin having the International Nomenclature of Cosmetic Ingredients (INCI) name Glycerin, purified water having the INCI name Water (Aqua), a chemical having the INCI name Methylglucoside Phosphate, and a chemical having the INCI name Copper Lysinate/Prolinate; a complex having the INCI name *Lactococcus* Ferment Lysate; acetyl hexapeptide-3; palmitoyl tripeptide, algae extract, dipalmitoyl hydroxyproline and/or Vitamin E Tocopherol; retinol and/or retinyl palmitate; hyaluronic acid; and a chemical having the INCI name Propanediol (and) *Orobanche rapum* Extract.

The first combination of active ingredients may include two or more items selected from the group consisting of glycyrrhetinic acid, tromethamine and/or *Usnea barbata* extract; *Chamomilla recutita* extract; and *Glycyrrhiza glabra* extract.

The first combination of active ingredients may include glycyrrhetinic acid, tromethamine and/or *Usnea barbata* extract; *Chamomilla recutita* extract; and *Glycyrrhiza glabra* extract.

In accordance with another embodiment, there is a method for producing a customized skin care product containing specified percentages by weight of two or more active ingredients suited for a customer's skin condition. The method includes receiving data indicative of a customer's skin condition, receiving premix data of a plurality of active ingredient premixes, each of the active ingredient premixes including a respective combination of active ingredients for treatment of skin, receiving premix dispenser data of a plurality of premix dispensers each of which is operable to dispense, by a single operation of the premix dispenser, a predefined quantity of a respective active ingredient premix from among the plurality of active ingredient premixes, receiving product base data of a plurality of skin care product bases, each of the skin care product bases having a respective form selected from the group consisting of cream, lotion, gel, and serum, receiving product base dispenser data of a plurality of product base dispensers each of which is operable to dispense, by a single operation of the product base dispenser, a predefined quantity of a respective skin care product base from among the plurality of skin care product bases, and generating a recipe for producing a customized skin care product containing specified percentages by weight of two or more active ingredients suited for the customer's skin condition. The recipe defines a number of operations of one or more of the plurality of premix dispensers and further defines a number of operations of a product base dispenser from among the plurality of product base dispensers.

The method may include receiving data indicative of a customer's skin type. Generating the recipe may include selecting a skin care product base from among the plurality of skin care product bases based on the data indicative of the customer's skin type.

The method may include receiving data indicative of a customer's preferred form for the customized skin care product, the preferred form selected from the group consisting of cream, lotion, gel, and serum. Generating the recipe may include selecting a skin care product base from among the plurality of skin care product bases based on the data indicative of the customer's preferred form for the customized skin care product.

The method may include operating the one or more of the plurality of premix dispensers according to the recipe to dispense respective quantities of one or more of the plurality of active ingredient premixes into a container, operating the product base dispenser according to the recipe to dispense a quantity of a skin care product base from among the plurality of skin care product bases into the container, and, after said operating the one or more of the plurality of premix dispensers and said operating the product base dispenser, mixing the contents of the container. The method may include, after said operating the one or more of the plurality of premix dispensers and said operating the product base dispenser, closing the container prior to said mixing.

In accordance with another embodiment, there is a non-transitory computer readable medium storing instructions executable by a processor to perform operations for producing a customized skin care product containing specified percentages by weight of two or more active ingredients suited for a customer's skin condition. The operations include receiving data indicative of a customer's skin condition, receiving premix data of a plurality of active ingredient premixes, each of the active ingredient premixes including a respective combination of active ingredients for treatment of skin, receiving premix dispenser data of a plurality of premix dispensers each of which is operable to dispense, by a single operation of the premix dispenser, a predefined quantity of a respective active ingredient premix from among the plurality of active ingredient premixes, receiving product base data of a plurality of skin care product bases, each of the skin care product bases having a respective form selected from the group consisting of cream, lotion, gel, and serum, receiving product base dispenser data of a plurality of product base dispensers each of which is operable to dispense, by a single operation of the product base dispenser, a predefined quantity of a respective skin care product base from among the plurality of skin care product bases, and generating a recipe for producing a customized skin care product containing specified percentages by weight of two or more active ingredients suited for the customer's skin condition. The recipe defines a number of operations of one or more of the plurality of premix dispensers and further defines a number of operations of a product base dispenser from among the plurality of product base dispensers.

In accordance with another embodiment, there is an active ingredient premix for producing a customized skin care product suited for treating hyperpigmentation. The active ingredient premix includes *Glycyrrhiza glabra* extract; *Bellis perennis* flower extract; kojic acid and/or hydroquinone; resveratrol; a peptide having the International Nomenclature of Cosmetic Ingredients (INCI) name Acetyl Glycyl Beta-Alanine; arbutin; and L-ascorbic acid.

In accordance with another embodiment, there is an active ingredient premix for producing a customized skin care product suited for treating skin prone to acne. The active ingredient premix includes niacinamide; salicylic acid; glycolic acid; argan oil or apricot kernel oil; a sediment having the International Nomenclature of Cosmetic Ingredients (INCI) name Silt; charcoal; and *Aloe barbadensis* concentrate.

In accordance with another embodiment, there is an active ingredient premix for producing a customized skin care product suited for improving the appearance of aging or scarred skin. The active ingredient premix includes a flavonoid complex including purified water having the International Nomenclature of Cosmetic Ingredients (INCI) name Water (Aqua), butylene glycol, *Ginkgo biloba* leaf extract, phenoxyethanol, and ethylhexylglycerin; green tea extract; vitamin E; dimethylaminoethanol (DMAE); Coenzyme $Q_{10}$; plant stem cell; and L-ascorbyl palmitate.

In accordance with another embodiment, there is an active ingredient premix for producing a customized skin care product suited for treating wrinkly skin. The active ingredient premix includes a complex of vegetable glycerin having the International Nomenclature of Cosmetic Ingredients (INCI) name Glycerin, purified water having the INCI name Water (Aqua), a chemical having the INCI name Methylglucoside Phosphate, and a chemical having the INCI name Copper Lysinate/Prolinate; a complex having the INCI name *Lactococcus* Ferment Lysate; acetyl hexapeptide-3; palmitoyl tripeptide; retinol and/or retinyl palmitate; hyaluronic acid; and a chemical having the INCI name Propanediol (and) *Orobanche rapum* Extract.

In accordance with another embodiment, there is an active ingredient premix for producing a customized skin care product suited for treating sensitive, red skin. The active ingredient premix includes glycyrrhetinic acid, tromethamine and/or *Usnea barbata* extract; *Chamomilla recutita* extract; and *Glycyrrhiza glabra* extract.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The present disclosure encompasses various embodiments of systems and methods for producing a customized skin care product containing specified percentages by weight of two or more active ingredients suited for a customer's skin condition. The detailed description set forth below in connection with the appended drawings is intended as a description of the several presently contemplated embodiments of these systems and methods, and is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
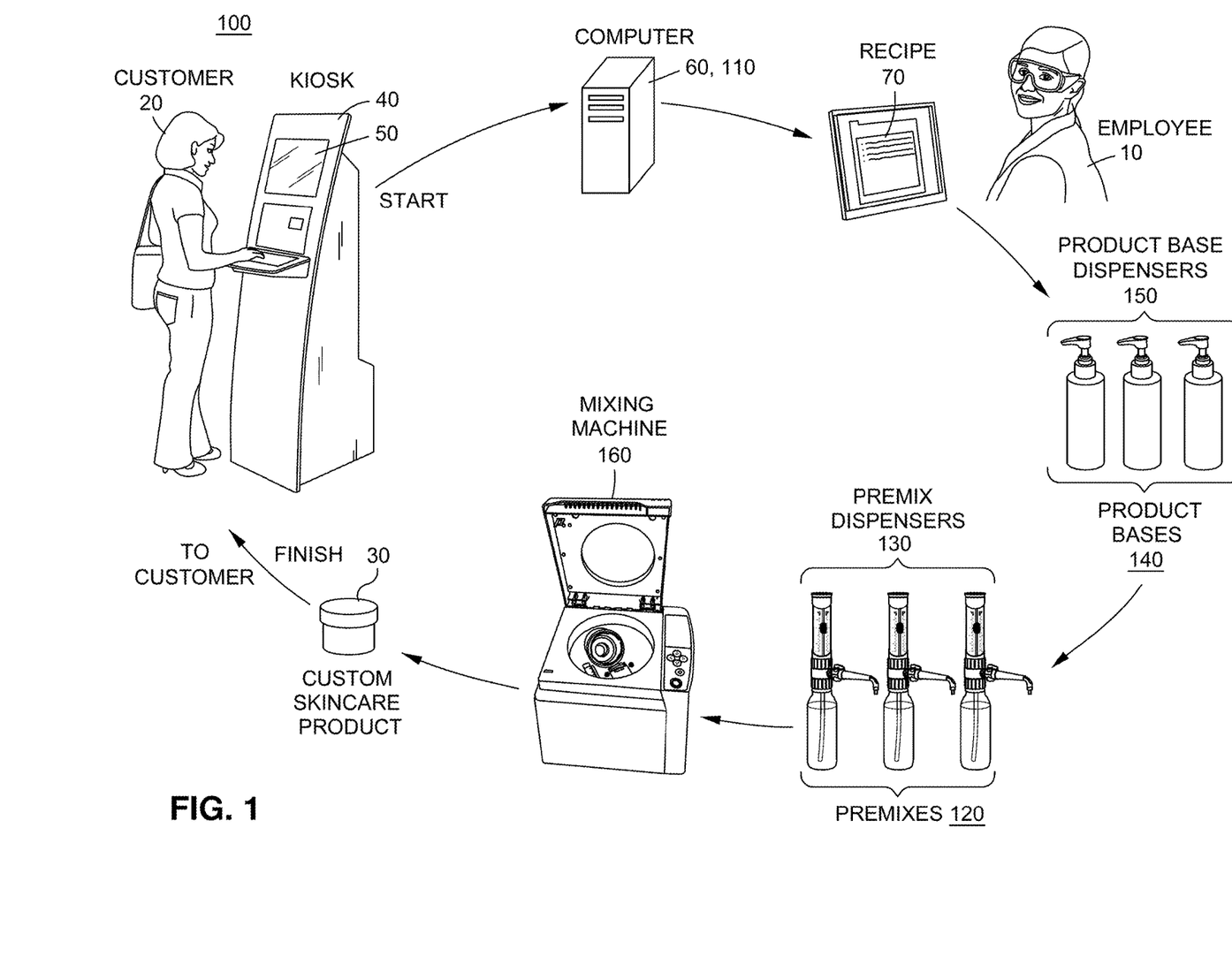
FIG. 1 shows an overview of a system according to an embodiment of the present disclosure in the context of a retail environment.

FIG. 1 shows an overview of a system 100 according to an embodiment of the present disclosure, in the context of a retail environment including a retail employee 10 and a customer 20 wishing to purchase a customized skin care product 30. In the example of FIG. 1, the customer 20 interacts (e.g. by touchscreen) with a kiosk 40 or other computer terminal in order to fill out a digital questionnaire 50. When the questionnaire 50 is completed, a computer 60 receives questionnaire data based on the customer's answers and generates a recipe 70 for producing a customized skin care product 30 suited to the customer. The recipe 70 may be printed or otherwise displayed to the employee 10, who will then produce the customized skin care product 30 according to the recipe.

In addition to the recipe generating software 110 running on the computer 60, the system 100 includes a plurality of active ingredient premixes 120, a corresponding plurality of premix dispensers 130, a plurality of product bases 140, a corresponding plurality of product base dispensers 150, and a mixing machine 160. The recipe generating software 110 is designed to generate the recipe 70 in terms of the premixes 120 and product bases 140 and their respective dispensers 130, 150 so that the recipe 70 is easy for the employee 10 to understand and the possibility for human error is minimized. To this end, each of the premixes 120 is prepared so that the relative quantities of each active ingredient in the premix 120 need not be considered and the premix 120 has a single final product weight percentage. Moreover, the employee 10 need not even consider the final product weight percentages of the premixes 120 because the premix dispensers 130 and product base dispensers 150 are each operable to dispense a predefined quantity by a single operation and the recipe generating software 110 generates the recipe 70 in terms of a number of dispenser operations for each dispenser 130, 150.

Having received the recipe 70, the employee 10 simply pumps or otherwise operates the dispensers 130, 150 according to the recipe 70 to fill a container with the ingredients of the custom skin care product 30. The employee 10 then closes the container and places it in the mixing machine 160. After a short time (e.g. less than 5 minutes, preferably less than 2 minutes, and most preferably less than 1 minute), the contents of the container are thoroughly mixed to produce the custom skin care product 30. The employee 10 may then simply hand the container containing the custom skin care product 30 to the customer 20 as part of a sale transaction.

The recipe generating software 110 may additional generate a label for the custom skin care product 30, e.g. in the form of a printed sticker. The label may include, for example, absolute or relative amounts of the ingredients of the product 30, including the active ingredients of the premix(es) 120 used in the product 30. The label may include warning information about the ingredients and directions for use of the product 30. The label may further include information about the source of the product 30, such as name and contact information of the retail store where the customer 20 purchased the product 30 and/or the company that produced the premixes 120 and other elements of the system 100, as well as any associated advertising material. Customers may have an option to receive such information, or a portion of such information, in an email instead of on a printed label, which may be more environmentally friendly as less paper needs to be printed. If the custom skin care product 30 is provided to the customer 20 prior to a sale transaction, the recipe generating software 110 may additionally generate a price tag, bar code, or other information to identify the product 30 and/or its price in the subsequent sale transaction. Alternatively, the recipe generating software 110 may directly communicate such information to sale transaction software at the time of generating the recipe 70 to automatically ring up the customer 20.

Figure 2:
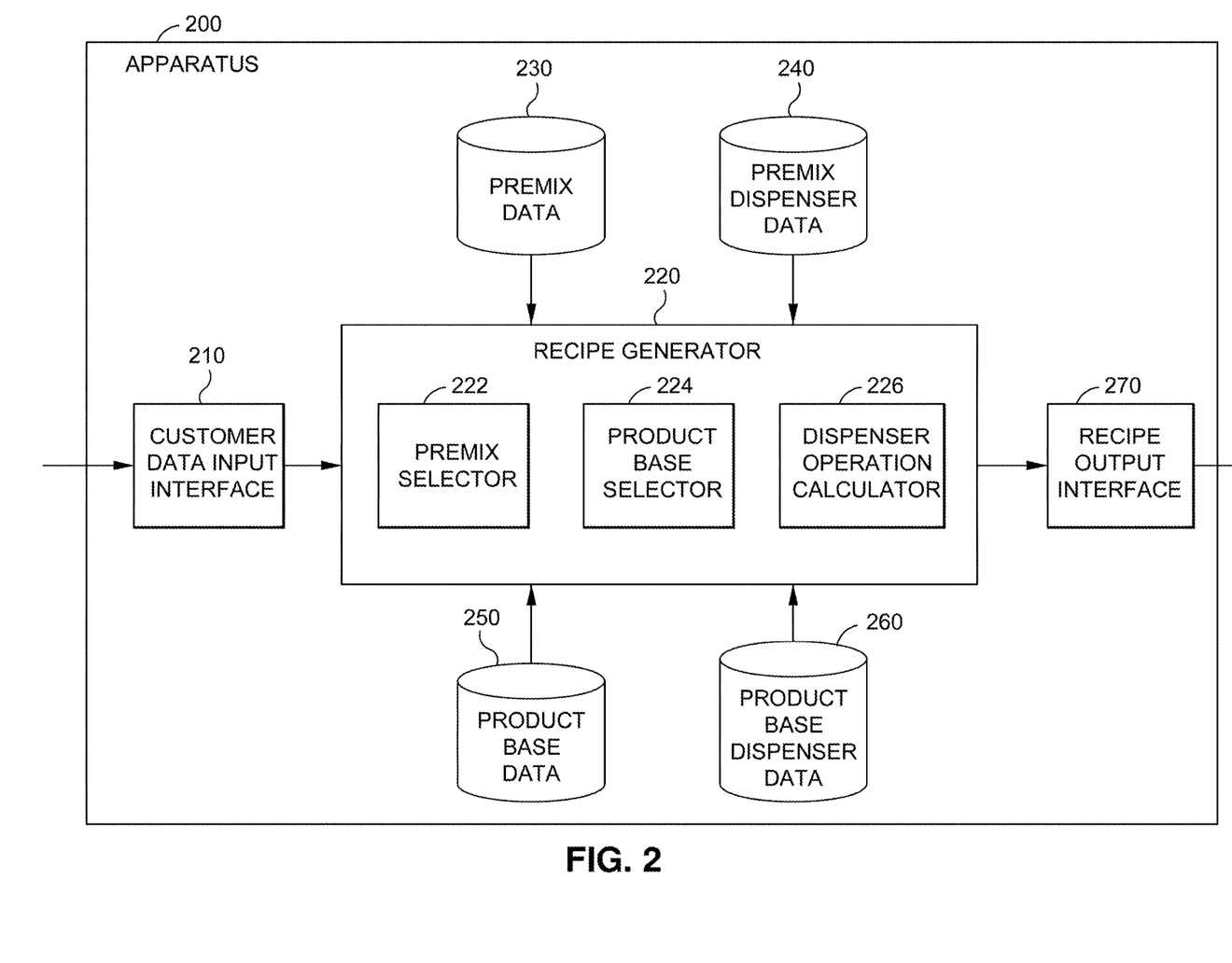
FIG. 2 shows an example apparatus for generating a recipe in accordance with the system of FIG. 1.

FIG. 2 shows an example apparatus 200 for generating a recipe 70 according to an embodiment of the disclosure. As described above, the recipe 70 may be generated by recipe generating software 110 run on a computer 60. In this respect, the apparatus 200 may be an example of the software 110 or may be an example of the computer 60 running the software 110. The apparatus 200 receives data indicative of a customer's skin condition and generates a recipe 70 for producing a customized skin care product 30 containing specified percentages by weight of two or more active ingredients suited for the customer's skin condition. The recipe 70 defines a number of operations of one or more of the premix dispensers 130 and a number of operations of one of the product base dispensers 150. The apparatus 200 may include a customer data input interface 210, a recipe generator 220, a premix data storage 230, a premix dispenser data storage 240, a product base data storage 250, a product base dispenser storage 260, and a recipe output interface 270.

The customer data input interface 210 receives data indicative of a customer's skin condition, such as data indicating one or more undesirable cosmetic or health-related conditions (e.g. hyperpigmentation, acne-prone skin, wrinkles, etc.) or desired effects (e.g. even skin tone, reduce occurrence of acne, improve wrinkles, etc.). The customer data input interface 210 may further receive data indicative of the customer's skin type (e.g. oily, dry, oily/dry, mature, thin, sensitive, etc.) and/or preferences with respect to product form (e.g. cream, lotion, gel, or serum), fragrance, sun protection, etc. Such skin condition data, skin type data, and/or preference data may be generated as the customer fills out a digital questionnaire 50 displayed on a screen of the kiosk 40. As the user interacts with the kiosk 40 to answer questions, make selections, indicate numerical degrees within specified ranges, etc., the customer data input interface 210 may quantify the user's responses and store the quantified values in a customer data file that further includes personal information of the customer 20 (e.g. identifying information, payment information, demographic information, etc.). Alternatively, the customer data file may be generated outside the apparatus 200 and the customer data input interface 210 may receive the customer data file.

It is contemplated that the customer data input interface 210 may include, control, or otherwise receive data from any of a variety of user interface devices including touch screen, keyboard, pointing device (e.g. mouse, trackball, touchpad), camera, voice commands, eye tracking, etc. For example, a camera may be used to take a picture of the customer's face. The customer's skin condition and/or skin type may be determined in part based on the picture. For example, the customer data input interface 210 may analyze image data of the customer's face to determine a degree of hyperpigmentation, blemishes, or wrinkly skin. The picture may also be used as identifying information of the customer. In a case where the data input interface 210 receives data from external user interface devices or receives a customer data file generated outside the apparatus 200, the data input interface 210 may receive such data by wired or wireless connection to an external device or removable storage medium (e.g. by USB or through a network such as the Internet, WAN, and/or LAN).

The recipe generator 220 generates a recipe for producing the custom skin care product 30 based on the customer data file. The recipe generator 220 may include a premix selector 222, a product base selector 224, and a dispenser operation calculator 226.

The premix selector 222 selects one or more of a plurality of available premixes 120 of the system 100 based on the skin condition data in the customer data file. The system 100 may include, for example, a first active ingredient premix 120A including a first combination of active ingredients for treatment of skin, a second active ingredient premix 120B including a second combination of active ingredients for treatment of skin that is different from the first combination of active ingredients, a third active ingredient premix 120C, and so on up to any number of active ingredient premixes 120. For example, the first active ingredient premix 120A may include a first combination of active ingredients for treatment of hyperpigmentation, the second active ingredient premix 120B may include a second combination of active ingredients for treatment of acne-prone skin, and the third active ingredient premix 120C may include a third combination of active ingredients for treatment of wrinkly skin. Additional contemplated skin conditions that may be treated by active ingredient premixes 120 include dehydrated skin, blackheads, whiteheads, blocked pores and follicles, acne scars, vascularity (telangiectasia or broken capillaries), flakiness, and low elasticity. Such information about what premixes 120 are available, including what conditions each available premix 120 treats, may be stored in the premix data storage 230. If the skin condition data in the customer data file indicates that the customer wishes to treat hyperpigmentation and wrinkly skin, the premix selector 222 may reference the premix data storage 230 and select premixes 120A and 120C accordingly.

In a simple example, the skin condition data in the customer data file may indicate binary values based on customer responses or image analysis (e.g. hyperpigmentation=yes; acne-prone skin=no; wrinkly skin=yes). The premix data storage 230 may then simply function as a lookup table, with each premix 120 stored in association with a corresponding skin condition. If the skin condition data indicates yes for a given skin condition, the premix selector 222 may consult the lookup table and find the premix 120 that corresponds to that skin condition. In a somewhat more complex example, the skin condition data in the customer data file may indicate values in the form of scores within ranges (e.g. hyperpigmentation=54; acne-prone skin=17; wrinkly skin=65, with each score out of 100). Each score may be derived from multiple questionnaire responses, image data, etc. in the customer data file. The premix selector 222 may compare each score to a threshold (e.g. a single universal threshold or individual thresholds stored in the premix data storage 230 for each premix 120) and select each premix 120 when the score for the skin condition associated with that premix 120 exceeds the relevant threshold. The premix selector 222 may further take into consideration any number of additional rules and restrictions, such as disallowed combinations of premixes 120 whose active ingredients should not be mixed, customer allergy or sensitivity information, etc.

The product base selector 224 selects one or more of a plurality of available product bases 140 of the system 100 based on the skin type data and/or preference data in the customer data file. The system 100 may include a plurality of product bases 140 that have different forms (e.g. cream, lotion, gel, serum, etc.) and/or are adapted for treatment of different skin types (e.g. oily, dry, combination oily/dry, etc.). For example, if the system 100 is configured for three different product base forms and three different skin types, there may be nine product bases 140A-140I, one for each combination of form and skin type (i.e. cream 140A for oily skin, cream 140B for dry skin, cream 140C for oily/dry skin, lotion 140D for oily skin, lotion 140E for dry skin, lotion 140F for oily/dry skin, gel 140G for oily skin, gel 140H for dry skin, and gel 140I for oily/dry skin). Information about what product bases 140 are available, including form of the product base 140 and/or skin type treated by the product base 140, may be stored in the product base data storage 250. If the skin type data in the customer data file indicates oily skin and the preference data in the customer data file indicates a preference for a cream, the product base selector 224 may reference the product base data storage 250 and select product base 140A accordingly.

As in the case of the premix selector 222 and premix data storage 230, it is envisioned that the selection of the product base 140 may be based on binary skin type data or based on skin type scores that fall within ranges, and the information stored in the premix data storage 230 may be organized accordingly. In the same way as a skin condition score, a skin type score may be derived from multiple questionnaire responses, image data, etc. in the customer data file. Also, like the premix selector 222, the product base selector 224 may further take into consideration any number of additional rules and restrictions, such as disallowed premix/base combinations, customer allergy information, etc.

The dispenser operation calculator 226 calculates a number of dispenser operations of the one or more premix dispensers 130 corresponding to the selected premix(es) 120 and a number of dispenser operations of the product base dispenser 150 corresponding to the selected product base 140. Each active ingredient within each premix 120 may have its own individual specified final product weight percentage, i.e. the percentage by weight that the active ingredient should appear in a final skin care product in order to be effective. However, as noted above, each of the premixes 120 is prepared ahead of time (e.g. in a laboratory setting) so that the relative quantities of each active ingredient in the premix 120 need not be considered and the premix 120 as a whole has a single final product weight percentage. As a simple example, a premix 120 may consist of three active ingredients a, b, c having specified final product weight percentages of 1%, 5%, and 10%, respectively. By preparing the premix 120 so that the three active ingredients are in proportion to their specified final product weight percentages, e.g. with five times as much (by weight) of active ingredient b as active ingredient a and twice as much (by weight) of active ingredient c as active ingredient b, the premix 120 as a whole may ensure that the individual specified final product weight percentages of each of the active ingredients a, b, c are simultaneously maintained in the final product.

Continuing with the above example, if the premix 120 has been prepared to have one part active ingredient a, five parts active ingredient b, and ten parts active ingredient c, then active ingredient a is $1/16$ of the premix 120, active ingredient b is $5/16$ of the premix 120, and active ingredient c is $10/16$ of the premix 120. The premix 120 itself thus has a single derived final product weight percentage of 16% as a whole, derived by adding up the total number of parts 1+5+10=16. When the premix 120 is 16% of the custom skin care product 30 (e.g. the other 84% being a product base 140), then active ingredient a will be 1% of the custom skin care product 30, active ingredient b will be 5% of the custom skin care product 30, and active ingredient c will be 10% of the custom skin care product 30. In this way, the individual specified final product weight percentages of 1%, 5%, and 10% will have been met when the premix 120 appears as 16% by weight of the final product.

For each of the premixes 120 whose data is stored in the premix data storage 230 (e.g. each premix 120 available to the system 100), the stored data may include an entry for the derived final product weight percentage of that premix 120. In the above example, the premix data storage 230 would store the value 16% in association with that premix 120. With one or more premixes 120 having been selected by the premix selector 222 and a product base 140 having been selected by the product base selector 224, the dispenser operation calculator 226 may reference such derived final product weight percentages stored in the premix data storage 230 for each premix 120 to determine the correct weights of each selected premix 230 and the selected product base 140 in the final product 30. For example, if a first premix 120 should be 16% of the final product 30 and a second premix 120 should be 10% of the final product 30, the first premix 120, second premix 120, and product base 140 may be combined at a weight ratio of 16/10/74 up to a designated total weight or a designated total volume determined by the size of a final product container. Absolute quantities of each premix 120 and product base 140 may be calculated based on such a designated total weight or volume. In this way, the dispenser operation calculator 226 may determine weight or volumetric quantities of each premix 120 and the product base 140 to be used in the custom skin care product 30.

The dispenser operation calculator 226 may then consult the premix dispenser data storage 240 and the product base dispenser data storage 260, which may store dispenser information for the premix dispensers 130 and product base dispensers 150, respectively. For example, the premix dispenser data storage 240 may store, for each premix dispenser 130 (each premix dispenser 130 corresponding to a single premix 120), a weight or volume of dispensed premix associated with a single pump, scoop, or other discrete dispenser operation of that premix dispenser 130. Similarly, the product base dispenser data storage 260 may store, for each product base dispenser 150 (each product base dispenser 150 corresponding to a single product base 140), a weight or volume of dispensed product base associated with a single pump, scoop, or other discrete dispenser operation of that product base dispenser 150. By referencing the premix dispenser data storage 240 and the product base dispenser data storage 260, the dispenser operation calculator 226 may convert the calculated absolute quantities (weight or volume) of each selected premix 120 and the selected product base 140 to a number of operations of each dispenser 130, 150. In this way, the recipe generator 220 may generate a recipe 70 for producing a customized skin care product 30 containing specified percentages by weight of two or more active ingredients suited for the customer's skin condition, the recipe 70 defining a number of operations of one or more premix dispensers 130 and further defining a number of operations of a product base dispenser 150.

If fragrances or other ingredients are to be included in the recipe 70, the recipe generator 220 may calculate absolute quantities and dispenser operations as above for each selected premix 120 and the selected product base 140 in addition to for any such other ingredients. In this case, the calculation may be adjusted accordingly to take into consideration the total weight or volume added by the additional ingredients.

An unskilled employee 10 may have difficulty reading gradations on a graded syringe or operating a scale in order to measure out the premixes 120 or product bases 140. Even in the case of a skilled employee 10, making such measurements throughout the day would inevitably result in human error that could have a detrimental effect on the quality of the custom skin care product 30. By generating a recipe 70 in terms of a number of discrete dispenser operations as described above, the system 100 may allow the employee 10 to prepare the custom skin care product 30 without needing to actually measure any of the ingredients. In this way, the preparation of the custom skin care product 30 may be considered "foolproof."

An example of a premix dispenser 130 that may be used to dispense a specific amount of a premix 120 per discrete dispenser operation is a bottle-top dispenser such as the Calibrex™ 520 line of bottle-top dispensers by Wheaton®, which may have a dispensing range of 1-10 mL in 0.25 mL steps with an inaccuracy of <±0.6-1.5% and an imprecision of <0.1-0.5%. Such bottle-top dispensers allow a specified amount of a bottle's contents to be dispensed per pump operation of the dispenser. Another example of a premix dispenser 130 is a single dosage capsule or packet, in which case a single discrete operation may be the opening of the capsule or packet and dumping of its contents (e.g. liquid or powder) into a container. An example of a single dosage capsule or packet is ActiCaps®. While such high-precision bottle-top dispensers and single dosage capsules or packets may also be used as a product base dispenser 150, precision is less critical in the case of the product bases 140 because the amount to be dispensed is typically much greater than that of the premixes 120. Therefore, it is contemplated that an ordinary pump bottle (as shown in FIG. 1) or pipette may be used for the product base dispensers 150, where the amount dispensed by each pump operation is known to within a somewhat greater range of error. Along the same lines, a hand-held scoop may be used, where each operation of the scoop dispenses approximately the same amount of the product base 140.

As explained above, because dispenser data of the premix dispensers 130 and product base dispensers 150 (e.g. the weight or volume associated with each dispenser operation) is stored in the premix dispenser data storage 240 and the product base dispenser data storage 260, the recipe generator 220 may define the recipe 70 in terms of dispenser operations. This allows the employee 10 to prepare the custom skin care product 30 without needing to make any actual measurements of the premixes 120 and product bases 140. Moreover, the premixes 120 themselves are each prepared so as to have a single derived final product weight percentage based on the specified final product weight percentages of the individual active ingredients constituting the premix 120. Because such derived final product weight percentages of the premixes 120 are stored in the premix data storage 230, the recipe generator 220 may calculate an amount of each ingredient (premix 120, product base 140, etc.) that results in the correct specified final product weight percentages of each individual active ingredient in the custom skin care product 30 without the employee 10 needing to even consider individual active ingredients.

The recipe output interface 270 outputs the recipe 70 generated by the recipe generator 220. Outputting the recipe 70 may include, for example, displaying the recipe 70 on a display screen and/or printing out the recipe 70 so that the employee 10 may view and follow the recipe 70 to produce the custom skin care product 30. Outputting the recipe 70 may further include storing the recipe 70, uploading the recipe 70 to a server, or otherwise making the recipe 70 available for later use, recordkeeping, sales analysis, etc. It is contemplated that the recipe output interface 220 may include, control, or otherwise exchange data with any of a variety of output interface devices including a printer, display screen, network interface, storage medium, etc.

As noted above, the recipe generating software 110 may additional generate a label for the custom skin care product 30 including, for example, absolute or relative amounts of the ingredients of the product 30, warning information, directions, product source information, etc. In this regard, the recipe generator 20 may further generate the information to be included in such a label, e.g. by referencing the premix data storage 230 and product base data storage 250 for additional information about the selected premix(es) 120 and product base 140. The recipe output interface 270 may output the label, e.g. to a label printer. It is also noted above that the recipe generating software 110 may generate a price tag, bar code, or other information to identify the product 30 and/or its price in a subsequent sale transaction, or may communicate such information to sale transaction software. In this case as well, the recipe generator 220 may generate the necessary information with reference to the premix data storage 230, product base data storage 250, or other data storage containing price information of the selected product components. The recipe output interface 270 may output such sale information, e.g. either to the label printer (in the case of a price tag, bar code, etc.) or to a network interface or other communication interface (in the case of communicating with sale transaction software running on an external device).

Figure 3:
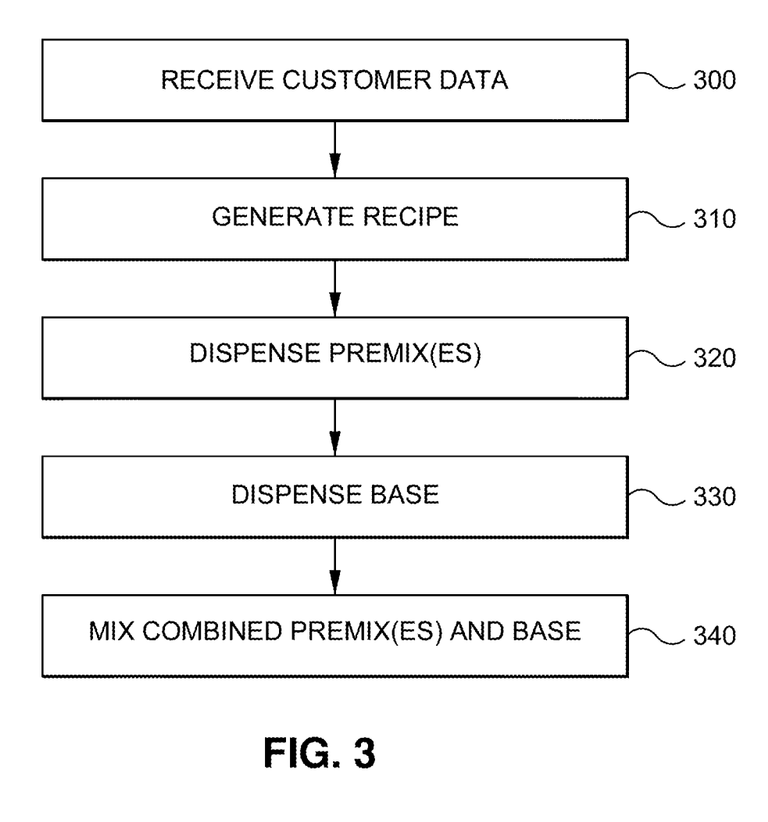
FIG. 3 shows an example operational flow for producing a custom skin care product using the system of FIG. 1.

FIG. 3 shows an example operational flow for producing a custom skin care product 30 using the system 100 of FIG. 1. For purposes of this example, the system 100 includes software 110 running on the computer 60 to cause the computer 60 to function as the apparatus 200 of FIG. 2. First, in a step 300, the system 100 receives customer data including skin condition data and skin type data of the customer 20. For example, in response to a user filing out a digital questionnaire 50 at a kiosk 40, the customer data input interface 210 of the apparatus 200 may receive skin condition data, skin type data, and other data (e.g. personal data) associated with the customer 20 and generate a customer data file. Then, in a step 310, the system 100 generates a recipe 70 based on the customer data. For example, the recipe generator 220 of the apparatus 200 may receive the skin condition data and skin type data, consult the premix data storage 230 and product base data storage 250 to select an appropriate combination of premix(es) 120 and product base 140, calculate the needed weight or volumetric amounts thereof, and consult the premix dispenser data storage 240 and product base dispenser data storage 260 to calculate numbers of dispenser operations for each of the selected premix(es) 120 and product base 140. The recipe output interface 270 of the apparatus 200 may then output a recipe 70 defining the respective numbers of operations.

With the recipe 70 having been output by the computer 60, e.g. as a display on a display screen or as a printed sheet of paper, the employee 10 then prepares the custom skin care product 30. In steps 320 and 330, the employee 10 dispenses the correct amounts of the premix(es) 120 and product base 140 by operating the appropriate premix dispensers 130 and product base dispenser 150 as instructed by the recipe 70. For example, the employee 10 may hold an empty product container underneath the product base dispenser 150 of the product base 140 listed in the recipe and pump or otherwise operate the product base dispenser 150 the number of times indicated in the recipe 70. The employee 10 may then move the product container underneath each of the premix dispenser(s) 130 of the premix(es) 120 listed in the recipe and pump or otherwise operate the premix dispenser(s) the number of times indicated in the recipe 70. Once the product container contains all of the ingredients set out in the recipe 70, the employee 10 may then close the product container and, in a step 340, mix the contents of the product container. For example, the employee 10 may place the closed container into the mixing machine 160 and press a "start" button on the mixing machine 160. When the mixing machine 160 has finished (e.g. a timer has expired and the mixing machine 160 automatically stopped functioning), the employee 10 may remove the finished custom skin care product 30 from the mixing machine 160. The mixing machine 160 may advantageously mix the contents of a closed container, e.g. by revolving and rotating the closed container, allowing for a mixing process that has no chance of contamination of the mixing machine 160 or surrounding area. An example of the mixing machine 160 is a Mazerustar® KK series mixer.

The closed container containing the custom skin care product 30 may be the same container that is thereafter sold to the customer 20. In a case where the apparatus 200 outputs a label to a label printer and/or a price tag, etc., the employee 10 may adhere such label, price tag, etc. to the container. The employee 10 may then hand the container containing the custom skin care product 30 to the customer 20, either as part of a sale transaction or prior to a sale transaction (e.g. where the sale is conducted at another location in the same store). An example of the product container is a dispenser-type container such as the MD® pump (offered by MEDISCA®), which may hold a 30 mL custom skin care product 30 and may have a clear view window, a snap-on actuator for dispensing the custom skin care product 30, and a lid. It is also contemplated that the custom skin care product 30 may be applied to the skin of the customer 20 using pledgets.

Figure 4:
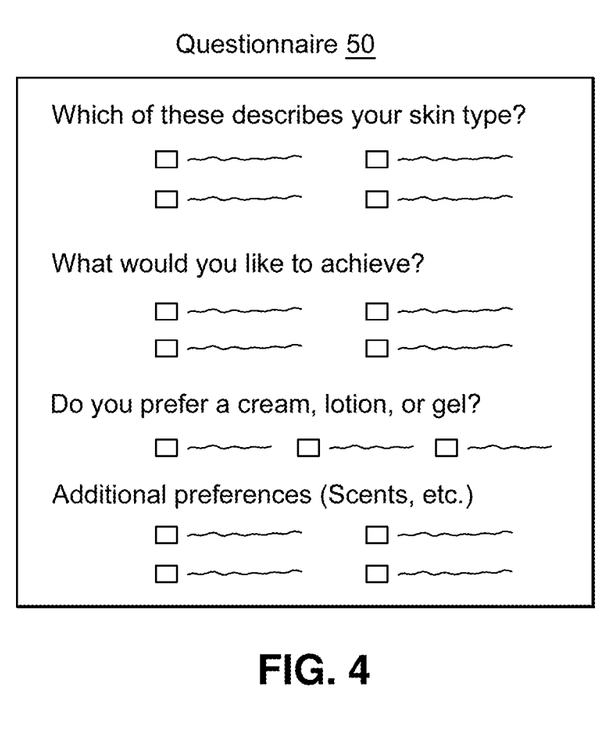
FIG. 4 shows an example questionnaire that may be used to generate customer data in accordance with the system of FIG. 1.

FIG. 4 shows an example questionnaire 50 that may be used to generate customer data in accordance with the system 100 of FIG. 1. The questionnaire 50 shown in FIG. 4 may be presented to the customer 20 on a display screen at a kiosk 40 or other computer terminal with a wired or wireless connection to the computer 60 running the recipe generating software 110, or may be presented to the customer 20 on the customer's own mobile device (e.g. smart phone) via a mobile application, allowing the customer 20 to order the custom skin care product 30 in advance. Alternatively, the questionnaire 50 may be a paper form that is filled out by the customer 20. The customer's responses on such a form may later be digitally scanned or manually entered, e.g. by the employee 10, to be received by the recipe generating software 110 (e.g. received by the customer data input interface 210 of the apparatus 200). In some cases, the customer 20 may provide questionnaire responses orally to the employee 10, who may then enter the customer data to the computer 60 on behalf of the customer 20.

As shown in the example questionnaire 50 of FIG. 4, the questionnaire 50 may include a series of questions with selectable responses (e.g. radio buttons or check boxes in the case of a digital questionnaire 50, fillable bubbles in the case of a paper questionnaire 50, etc.). For example, selectable responses to the question "Which of these describes your skin type?" might include "oily," "dry," and "combined oily/dry." In some cases, selections may be made from ranges of values. For example, the questionnaire 50 may pose the question "On a scale of 1 to 10, how oily is your skin?" and provide selectable responses 1-10. The questionnaire 50 may include one or more questions such as these designed to determine the skin type of the customer 20, whose responses may be used by the product base selector 224 in selecting a product base 140. The selection of a product base 140 by the product base selector 224 may also be based on questions about the customer's preferences, e.g. "Do you prefer a cream, lotion, or gel?" The questionnaire 50 may also include one or more questions designed to determine the skin condition of the customer 20, for example, "What would you like to achieve?" with possible answers including "even skin tone," "reduce occurrences of acne," "improve wrinkles," etc. Responses to such questions may be used by the premix selector 222 in selecting one or more premixes 120. As part of filling out the questionnaire 50, a camera connected to the kiosk 40 or other computer terminal may capture an image of the customer 20, e.g. the customer's face, which may also be used by the premix selector 222 in selecting one or more premixes 120. The questionnaire 50 may also ask the customer 20 about additional preferences (e.g. with or without fragrance, etc.), which may further be used by the recipe generator 220 to generate the recipe 70. For example, the recipe 70 may include additional components (e.g. an ingredient to provide a preferred fragrance or sun protection) to meet the preferences of the customer 20. The questionnaire 50 may also prompt the customer 20 to enter personal information of the customer 20 (e.g. identifying information, payment information, demographic information, etc.).

Figure 5:
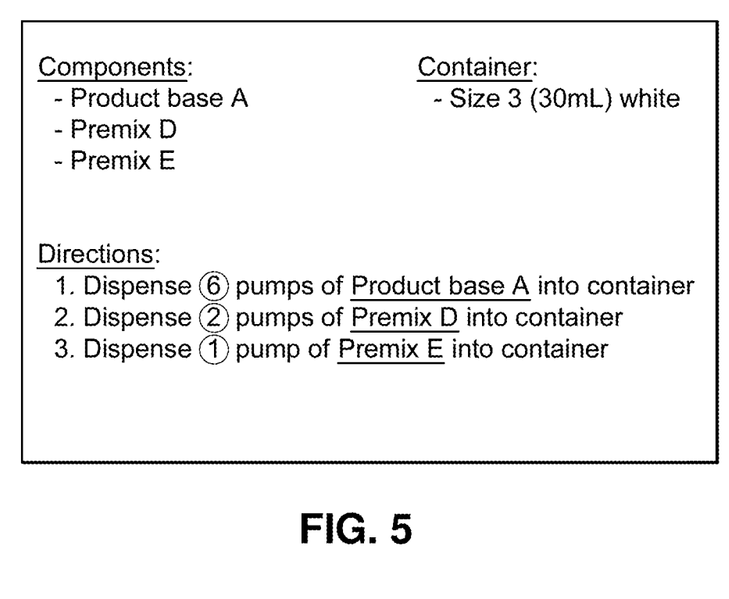
FIG. 5 shows an example recipe that may be generated by the system of FIG. 1.

FIG. 5 shows an example recipe 70 that may be generated by the system 100 of FIG. 1. The recipe 70 may be generated by the recipe generator 220 and output by the recipe output interface 270, e.g. displayed on a screen or printed out by a printer connected to the computer 60 running the recipe generating software 110. The example recipe 70 of FIG. 5 includes a list of components ("Product base A," "Premix D," "Premix E") and an indication that a "Size 3 (30 mL) white" container should be used. The recipe 70 further includes a list of directions to produce the custom skin care product 30, as set forth in steps 1, 2, and 3. As explained above, the recipe 70 may be generated in terms of a number of discrete operations of the premix dispensers 130 associated with selected premixes 120 and the product base dispensers 150 associated with the product bases 140. Thus, as shown, the recipe 70 may simply indicate "Dispense 6 pumps of Product base A into container," etc., without providing any indication of weight or volumetric measurements. Even an untrained employee 10 can follow such a simple recipe with little possibility of error.

In a simple example, only a single size (e.g. 30 mL or 1 fluid ounce), color, etc. may be used for all containers of the system 100, which may have the advantage of simplicity and reduce possibility of human error. In this case, the indication of a "Size 3 (30 mL) white" container in FIG. 5 may be omitted. It is also envisioned that the indication of a "Size 3 (30 mL) white" container may refer to one of a plurality of possible containers available to the system 100. For example, there may be container sizes numbered 1, 2, and 3 for holding different volumes of custom skin care product 30. The containers may also come in a variety of colors (e.g. "white") or have other optional features. When filling out the questionnaire 50, the customer 20 may be prompted with questions that determine the attributes of the container (e.g. "What size would you like?"), and the recipe generator 220 may take this information into account when generating the recipe 70, listing the correct container in the recipe 70 based on the choices made by the customer 20. As noted above, the recipe generator 220 may calculate the absolute quantities of each premix 120 and product base 140 to be included in the custom skin care product 30 based on a designated total weight or a designated total volume determined by the size of a final product container. In a case where different size containers are available, a selection of a desired size by the customer 20 may set the designated total weight or designated total volume for this calculation.

Less complicated and more complicated versions of the recipe 70 are contemplated as well. A less complicated version of the recipe 70 may omit the component list and include a simple table in place of steps 1, 2, and 3 of FIG. 5. For example, a simple two-column table may have components ("Product base A," "Premix D," "Premix E" in one column and corresponding numbers of pumps ("6", "2", "1") in the other. A more complicated version of the recipe 70 may include detailed weight, volume, active ingredient, or other information associated with the components of the recipe 70. In order to make the recipe 70 as easy to understand as possible, such detailed information is preferably presented in smaller type-face, in the case of a printed recipe 70, or in an initially hidden form, in the case of a recipe 70 displayed on a display screen. For example, if a recipe 70 is displayed on a display screen, the employee 10 may input commands (e.g. by mouse, touch screen, etc.) to select a part of the recipe 70 where detailed information is desired. Selectable parts of the recipe 70 may be, for example, the circled numbers and underlined components shown in the steps of the recipe 70 of FIG. 5. Selecting a part of the recipe 70 may expand a collapsible block of text, display a popup window, or otherwise allow the employee 10 to "drill down" for detailed information.

The recipe 70 may further include personal information of the customer 20, which may be useful for identifying the customer 20 from among multiple customers for purposes of a subsequent sale transaction. For example, if an image of the customer 20 is captured by a camera as part of filling out the questionnaire 50, the picture of the customer 20 may appear at the top of the recipe 70 along with the customer's name. Identifying information of the recipe 70 or transaction may also be included. For example, the recipe 70 may include a unique "customer number" that increments for every recipe generated and resets at the beginning of each day.

Figure 6:
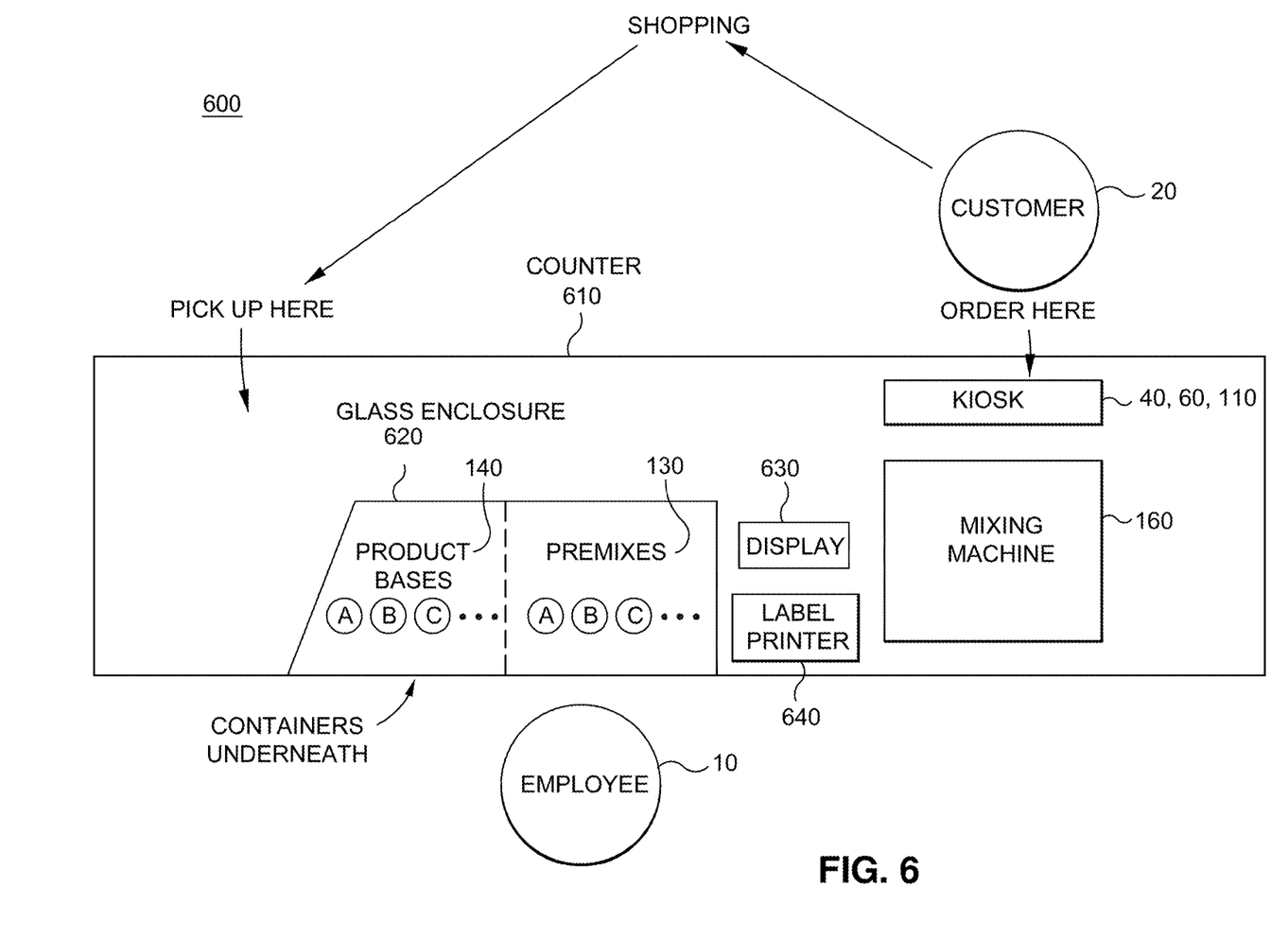
FIG. 6 shows a schematic overhead view of an example retail environment in which the system of FIG. 1 may be implemented.

FIG. 6 shows a schematic overhead view of an example retail environment 600 in which the system 100 may be implemented. As shown, the system 100 may fit on a counter 610 in a retail store, such as a store that sells off-the-shelf skin care products in addition to providing the custom skin care products 30 of the present disclosure. On the counter 610, there may a glass enclosure 620 like at a juice bar or sandwich shop, allowing customers to watch the custom skin care product 30 being made while keeping the custom skin care product 30 free of germs. The glass enclosure 620 may be any transparent material, including non-glass materials such as plastic, e.g. poly(methyl methacrylate), such as a material known by the trade name Plexiglas. Behind the glass enclosure 620 may be a row of product bases 140 labeled "A", "B", "C", etc. and a row of premixes 130 labeled "A", "B", "C", etc. Such "A", "B", "C" labels may correspond to the terminology used in the recipe 70 (see FIG. 5). Other ingredients (e.g. fragrances) may also be set up behind the glass enclosure 620. The workspace behind the glass enclosure 620 may be organized like an assembly line so that the employee 10 can move from one area to the next while combining ingredients to produce a custom skin care product 30. Containers for the custom skin care product 30, which may come in different sizes, colors, etc., may be organized on shelves underneath the counter 610 for easy access by the employee 10. The counter 610 may further provide a space for the kiosk 40, which may include the computer 60 running recipe generating software 110, as well as a display 620 connected to the computer 60, a label printer 630 connected to the computer 60, and the mixing machine 160.

When a customer 20 wishes to place an order for a custom skin care product 30, the customer 20 may approach the counter 610 and fill out a digital questionnaire 50 on the kiosk 40 as described above. Based on the customer's responses to the questionnaire 50, the computer 60 running recipe generating software 110 may function as the apparatus 200 of FIG. 2 to receive the customer data from the kiosk 40, generate a recipe 70, and output the recipe 70 to be displayed on the display 620. The employee 10 can see the recipe 70 on the display 620 and, in some cases, can interact with the recipe 70 by touch screen or other input device to drill down to more detailed information if necessary. The computer 60, functioning as the apparatus 200, may further output label data and/or sale data to the label printer 640, which may then print an appropriate label, price tag, etc. for the custom skin care product 30.

Following the recipe 70, the employee 10 may grab the correct container from underneath the counter 610 and fill the container with the correct amounts of the indicated product base 140 and premix(es) 130 by operating the product base dispensers 150 and premix dispensers 130 as instructed in the recipe 70. While preparing the custom skin care product 30, the employee 10 may simultaneously view the recipe 70 because of the convenient position of the display 630 on the counter 610. With the container filled as instructed by the recipe 70, the employee 10 may then close the container (e.g. attach a snap-on actuator and/or lid in the case of an dispenser-type container such as the MD® pump), place the closed container in the mixing machine 160, and run the mixing machine 160. The mixing process may take less than 5 minutes, preferably less than 2 minutes, and most preferably less than 1 minute. In a simple example, the mixing time may not vary and may be set to a single value, e.g. 2 minutes. This may be particularly effective in a case where only a single size container is used, e.g. 30 mL or 1 fluid ounce, and may have the advantage of simplicity and reduced possibility of human error.

It is also envisioned that the mixing time may be variable and may, for example, depend on the form of the selected product base 140 (e.g. cream, lotion, gel, or serum) and/or the size of the container. Based on such information, the recipe generator 220 of the apparatus 200 may calculate the mixing time and include it in the recipe 70 (e.g., in the example of FIG. 5: "4. Place container in mixing machine and set time to 1:30"). In this way, the recipe 70 may define a mixing time. The employee 10 may then adjust the mixing time by operating the mixing machine 160 according to the recipe 70.

When the mixing is finished, the employee 10 may remove the container from the mixing machine 160, affix a label, price tag, etc. printed by the label printer 640 to the container, and place the container containing the finished custom skin care product 30 in a "pick-up" area of the counter 610. The employee 10 may then call the name of the customer 20 or display the customer number of the customer 20 to notify the customer 20 that the custom skin care product 30 is ready to be picked up.

During the time that the employee 10 is preparing the custom skin care product 30, e.g. after the customer 20 finishes filling out the questionnaire 50 on the kiosk 40, the customer 20 may either watch the process through the glass enclosure 620 or leave the counter 610 and do some shopping. The custom skin care product 30 may be made in front of the customer 20 while the customer 20 waits. When the custom skin care product 30 is ready to be picked up, the customer 20 may return to the counter 610 and take the custom skin care product 30. The customer 20 may, for example, compare a customer number printed by the kiosk 40 with a customer number displayed next to the custom skin care product 30 in the pick-up region of the counter. The customer 20 may then bring the custom skin care product 30 to a separate checkout counter of the retail environment 600 to complete a sale transaction.

As described above, the entire system 100 is small enough to reside on a counter 610 in a store. In addition, the process takes very little time (e.g. less than five minutes) from the time that the customer 20 first places the order at the kiosk 40 to the time that the customer 20 receives the custom skin care product 30. These qualities make the system 100 uniquely suited for a retail environment 600, where conventional services offering custom skin care products may require communication and shipment to and from a laboratory setting, making it difficult to address an urgent need for skin care. Furthermore, because there is no shipping time involved, it is okay that the custom skin care product 30 made according to the system 100 has a relatively short shelf life. Therefore, the custom skin care product 30 can be made fresh, without any preservatives that might detrimentally affect a person's health or the environment. The custom skin care product 30 may be made in compliance with standards for labeling as organic.

The active ingredient premixes 120 may include a hyperpigmentation mix suited for treating hyperpigmentation of the skin. The hyperpigmentation mix may include *Glycyrrhiza glabra* extract, having a specified final product weight percentage of 4-10%. *Glycyrrhiza glabra* extract is a skin lightening agent and has been shown, in addition to the skin lightening effect, to soothe skin and have rejuvenating and anti-irritant effects. The hyperpigmentation mix may include *Bellis perennis* flower extract, such as an extract sold under the trade name Belides™ or Belides™ (NP), having a specified final product weight percentage of 1-5%. *Bellis perennis* flower extract has a skin lightening effect and reduces color intensity of age spots. The hyperpigmentation mix may include kojic acid (e.g. CAS Number 501-30-4) or a mix of kojic acid and hydroquinone (e.g. CAS Number 123-31-9), having a specified final product weight percentage of 1-3%. Kojic acid and hydroquinone are skin lightening agents. The hyperpigmentation mix may include resveratrol (e.g. CAS Number 501-36-0), having a specified final product weight percentage of 0.1-1%. Resveratrol has skin lightening and skin brightening effects. The hyperpigmentation mix may include a peptide having the International Nomenclature of Cosmetic Ingredients (INCI) name Acetyl Glycyl Beta-Alanine, such as that sold under the trade name GenoWhite™, having a specified final product weight percentage of 0.5-2%. Acetyl Glycyl Beta-Alanine has a skin-lightening effect and reduces darkness of age spots. The hyperpigmentation mix may include arbutin (e.g. CAS Number 497-76-7), having a specified final product weight percentage of 0.5-2%. Arbutin has a skin lightening effect and reduces darkness of age spots. The hyperpigmentation mix may include L-ascorbic acid (e.g. CAS Number 50-81-7), having a specified final product weight percentage of 5-20%. L-ascorbic acid has a skin lightening effect and may help prevent and/or treat damage caused by ultraviolet radiation. The relative quantities of each active ingredient in the hyperpigmentation mix may be controlled so that the hyperpigmentation mix as a whole maintains a single final product weight percentage, for example, by mixing the active ingredients in proportion to their individual specified final product weight percentages. The hyperpigmentation mix may include two or more of the above seven active ingredients, may include all of the above seven active ingredients, or may consist essentially or exclusively of the above seven active ingredients. The hyperpigmentation mix may have topical, lotion, gel, mask, cream, and fluid applications.

The active ingredient premixes 120 may include an acne prone mix suited for treating skin prone to acne. The acne prone mix may include niacinamide (e.g. CAS Number 98-92-0), having a specified final product weight percentage of 1-6%. Niacinamide has been found to have soothing activity which may be useful for blemished skin. The acne prone mix may include salicylic acid (e.g. CAS Number 69-72-7), having a specified final product weight percentage of 0.1-5%. Salicylic acid is an ingredient for skin peels and in products for oily, acneic, and/or blemished skin. The acne prone mix may include glycolic acid (e.g. CAS Number 79-14-1), having a specified final product weight percentage of 5-20%. Glycolic acid is an ingredient for skin peels and in products for oily, acne-prone, and/or blemished skin. The acne prone mix may include lactic acid (e.g. CAS Number 50-21-5), having a specified final product weight percentage of 5-10%. Lactic acid sheds off the outermost layer of skin cells (corneocytes) and induces renewal of a skin cell layer. The acne prone mix may include argan oil or apricot kernel oil, having a specified final product weight percentage of 1-4%. Argan oil or apricot kernel oil is a natural emollient with excellent nutritional benefits for skin. The acne prone mix may include a sediment having the INCI name Silt, such as that sold under the trade name Sulphur Mud, having a specified final product weight percentage of 2-20%. Silt has great absorbing power and is very useful for greasy, blemished, and impure skin. The acne prone mix may include charcoal, having a specified final product weight percentage of 1-10%. Fine porous charcoal is able to adsorb impurities and oil on skin and hair. The acne prone mix may include *Aloe barbadensis* concentrate, having a specified final product weight percentage of 1-10%. *Aloe barbadensis* concentrate is a potent moisturizer. The relative quantities of each active ingredient in the acne prone mix may be controlled so that the acne prone mix as a whole maintains a single final product weight percentage, for example, by mixing the active ingredients in proportion to their individual specified final product weight percentages. The acne prone mix may include two or more of the above seven active ingredients, may include all of the above seven active ingredients, or may consist essentially or exclusively of the above seven active ingredients. The acne prone mix may have topical, cream, lotion, gel, and shampoo applications.

The active ingredient premixes 120 may include an antioxidant blend suited for improving the appearance of aging or scarred skin. The antioxidant blend may include a flavonoid complex including purified water having the INCI name Water (Aqua), butylene glycol (e.g. CAS Number 107-88-0), *Ginkgo biloba* leaf extract, phenoxyethanol (e.g. CAS Number 122-99-6), and ethylhexylglycerin, having a specified final product weight percentage of 5-10%. The antioxidant blend may include green tea extract such as an extract of *Camellia sinensis* leaves, having a specified final product weight percentage of 0.1-2%. Green tea extract is a potent antioxidant agent. The antioxidant blend may include vitamin E, having a specified final product weight percentage of 0.5-2.5%. Vitamin E is a potent antioxidant. The antioxidant blend may include dimethylaminoethanol (DMAE) (e.g. CAS Number 108-01-0), having a specified final product weight percentage of up to 5%. DMAE helps to tighten skin, reduce sagging, and improve firmness. The antioxidant blend may include Coenzyme $Q_{10}$ (e.g. CAS Number 303-98-0), having a specified final product weight percentage of 2-6%. Coenzyme $Q_{10}$ is a potent antioxidant and can significantly reduce the appearance of aged skin and wrinkles. The antioxidant blend may include plant stem cell, having a specified final product weight percentage of 2-4%. Plant stem cell is used in anti-aging preventive products. The antioxidant blend may include L-ascorbyl palmitate (e.g. CAS Number 137-66-6), having a specified final product weight percentage of 0.5-8%. L-ascorbyl palmitate is a potent antioxidant and can improve the appearance of aged skin. The relative quantities of each active ingredient in the antioxidant blend may be controlled so that the antioxidant blend as a whole maintains a single final product weight percentage, for example, by mixing the active ingredients in proportion to their individual specified final product weight percentages. The antioxidant blend may include two or more of the above seven active ingredients, may include all of the above seven active ingredients, or may consist essentially or exclusively of the above seven active ingredients. The antioxidant blend may have topical, cream, lotion, gel, and mask applications.

The active ingredient premixes 120 may include an improve wrinkle mix suited for treating wrinkly skin. The improve wrinkle mix may include a complex of vegetable glycerin having the INCI name Glycerin, purified water having the INCI name Water (Aqua), a chemical having the INCI name Methylglucoside Phosphate, and a chemical having the INCI name Copper Lysinate/Prolinate, such as a complex sold under the trade name Neodermyl®, having a specified final product weight percentage of 0.1-0.2%. Such a complex has an anti-wrinkle effect, functions as a youth collagen booster, and firms, re-densifies, and energizes skin. The improve wrinkle mix may include a complex obtained from a lysate of *Lactococcus lactis*, such as a complex sold under the trade name ProRenew Complex CLR™ and having the INCI name *Lactococcus* Ferment Lysate, having a specified final product weight percentage of 3%. ProRenew Complex CLR has a probiotic skin renewal effect. The improve wrinkle mix may include acetyl hexapeptide-3, having a specified final product weight percentage of 5-10%. Acetyl hexapeptide-3 is used in anti-aging and anti-wrinkle creams and lotions. The improve wrinkle mix may include palmitoyl tripeptide (e.g. palmitoyl tripeptide-5, palmitoyl tripeptide-38), having a specified final product weight percentage of 2-4%. Palmitoyl tripeptide is used in anti-aging and anti-wrinkle creams. The improve wrinkle mix may include algae extract (e.g. an algae extract having the INCI name *Laminaria* (Algae) extract in a base of glycerin and water), having a specified final product weight percentage of 5-10%. The improve wrinkle mix may include dipalmitoyl hydroxyproline (e.g. CAS Number 41672-81-5), having a specified final product weight percentage of 2%. The improve wrinkle mix may include Vitamin E Tocopherol, e.g. alpha tocopherol (e.g. CAS Number 59-02-9) such as dl-alpha tocopherol, having a specified final product weight percentage of 0.4%. The improve wrinkle mix may include retinol (e.g. CAS Number 68-26-8), having a specified final product weight percentage of up to 5%, and/or retinyl palmitate (e.g. CAS Number 79-81-2), having a specified final product weight percentage of 1%. Retinol and retinyl palmitate have anti-wrinkle and anti-aging properties. The improve wrinkle mix may include hyaluronic acid (e.g. CAS Number 9004-61-9), having a specified final product weight percentage of 0.1-15%. Hyaluronic acid exhibits anti-wrinkle effects. The improve wrinkle mix may include a chemical having the INCI name Propanediol (and) *Orobanche rapum* Extract, such as a chemical sold under the trade name Revivyl™, having a specified final product weight percentage of 0.5%. Revivyl™ exhibits skin renewal activation, skin regeneration, skin resurfacing, anti-ageing, and anti-wrinkle effects, and may be used to treat dry skin. The relative quantities of each active ingredient in the improve wrinkle mix may be controlled so that the improve wrinkle mix as a whole maintains a single final product weight percentage, for example, by mixing the active ingredients in proportion to their individual specified final product weight percentages. The improve wrinkle mix may include two or more of the above ten active ingredients, may include all of the above ten active ingredients, or may consist essentially or exclusively of the above ten active ingredients. The improve wrinkle mix may have topical, cream, lotion, gel, and mask applications.

The active ingredient premixes 120 may include a sensitive red skin mix suited for treating sensitive, red skin. The sensitive red skin mix may include a combination of glycyrrhetinic acid (e.g. CAS Number 471-53-4), tromethamine (e.g. CAS Number 77-86-1), and/or *Usnea barbata* extract, having a specified final product weight percentage of 2-5%. Such a combination has an anti-inflammatory effect. The sensitive red skin mix may include *Chamomilla recutita* extract, having a specified final product weight percentage of 1-4%. *Chamomilla recutita* extract has a soothing effect. The sensitive red skin mix may include *Glycyrriza glabra* extract, having a specified final product weight percentage of 3-5%. *Glycyrrhiza glabra* extract has anti-irritant and soothing effects. The relative quantities of each active ingredient in the sensitive red skin mix may be controlled so that the sensitive red skin mix as a whole maintains a single final product weight percentage, for example, by mixing the active ingredients in proportion to their individual specified final product weight percentages. The sensitive red skin mix may include two or more of the above three active ingredients, may include all of the above three active ingredients, or may consist essentially or exclusively of the above three active ingredients. The sensitive red skin mix may have topical, cream, lotion, gel, mask, and scalp applications.

The choice of active ingredients and amounts thereof in each of the active ingredient premixes 120 may be selected such that the active ingredient premixes 120 can safely be applied to skin without causing harmful effects. In this way, if the custom skin care product 30 is prepared incorrectly, the erroneous custom skin care product 30 will not cause harm to the skin of the customer 20. Similarly, the employee 10 may safely handle the active ingredient premixes 120 when preparing the custom skin care product 30 for the customer 20, without any danger in the event of a spill.

As noted above, the apparatus 200 may be an example of the software 110. More specifically, the apparatus 200 may be an example of any combination of the software 110 and hardware components of the computer 60, including purely software and purely hardware combinations. The software 110, and likewise any software components of the apparatus 200, may be recorded on a non-transitory computer-readable medium. A processor of the computer 60 may execute the software 110 to cause the computer 60 to function as the apparatus 200. The computer 60 may be a desktop computer or a mobile device such a smart phone or tablet, in which case the software 110 may be a mobile application or "app." Alternatively, the apparatus 200 may be embodied in dedicated circuitry or in a combination of programmable circuitry (e.g. field-programmable gate array, programmable logic array) and executable state information thereof. It is envisioned that such non-software embodiments of the apparatus 200 may be used in the system 100 in addition to or in place of the software 110 running on the computer 60.

Software-as-a-service (Saas) and other cloud-based models of the software 110 and apparatus 200 are also envisioned. For example, the apparatus 200 may be embodied in a thin client or web browser functioning as the customer data input interface 210 and recipe output interface 270, with all or a portion of the recipe generator 220 and data storages 230, 240, 250, 260 located in the cloud (e.g. on an external server). In this regard, as used throughout this disclosure, generating the recipe 70 may refer to communicating with such external recipe generator 200 and data storages 230, 240, 250, 260.

Non-electronic embodiments of the apparatus 200 are also envisioned. For example, the apparatus 200 may be a mechanical device such as a stack of paper wheels that rotate relative to each other about one or more axes. The employee 10 (or the customer 20) may input the customer data by turning one or more of the wheels to positions corresponding to specific questionnaire responses. The recipe 70 may be output in the form of text that becomes visible or highlighted as a result of the input, for example, text that is aligned with a cut-out viewing window in one of the paper wheels. It is envisioned that such embodiments of the apparatus 200 may be used in the system 100 in addition to or in place of the software 110 running on the computer 60 and/or the kiosk 40.

As described above, the apparatus 200 may output a recipe 70 and the employee 10 may follow the recipe to prepare the custom skin care product 30. It is also envisioned that various tasks of the employee 10 may be automated. For example, rather than the employee 10 operating premix dispensers 130, a machine may be provided having hoppers for receiving each active ingredient premix 120 and/or product base 140. When the recipe 70 is generated, valves of the hoppers may be controlled automatically, e.g., by an electrical signal generated by the apparatus 200, to dispense appropriate amounts of each premix 120 and/or base 140 in accordance with the recipe 70 into the container. The employee 10 may then simply close the container and proceed with placing the container in the mixing machine 160. It is noted that a hopper design may also be implemented with manual control by the employee 10, in which case each hopper may function as a dispenser 130, 150 operated by the push of a button or other manual operation to dispense an amount of premix 120 or base 140 into the container.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for producing a customized skin care product containing specified percentages by weight of two or more active ingredients suited for a customer's skin condition, the method comprising:

receiving data indicative of a customer's skin condition;

receiving premix data of a plurality of active ingredient premixes, each of the active ingredient premixes including a respective combination of a plurality of active ingredients for treatment of skin;

receiving premix dispenser data of a plurality of premix dispensers each of which is operable to dispense, by a single operation of the premix dispenser, a predefined quantity of a respective active ingredient premix from among the plurality of active ingredient premixes;

receiving product base data of a plurality of skin care product bases, each of the skin care product bases having a respective form being any one of cream, lotion, gel, and serum;

receiving product base dispenser data of a plurality of product base dispensers each of which is operable to dispense, by a single operation of the product base dispenser, a predefined quantity of a respective skin care product base from among the plurality of skin care product bases;

generating a recipe for producing a customized skin care product containing specified percentages by weight of two or more active ingredients suited for the customer's skin condition, the recipe defining a number of operations of at least two of the plurality of premix dispensers and further defining a number of operations of a product base dispenser from among the plurality of product base dispensers;

providing the plurality of active ingredient premix dispensers having the plurality of active ingredient premixes, wherein any one of the plurality of active ingredient premixes is mixable with any one of the plurality of product bases;

operating the one or more of the plurality of premix dispensers according to the recipe to dispense respective quantities of one or more of the plurality of active ingredient premixes into a container;

providing the plurality of product base dispensers having the plurality of product bases, wherein a first skin care product base of the plurality of product bases has a different respective form from a second skin care product base of the plurality of product bases;
operating the product base dispenser according to the recipe to dispense a quantity of a skin care product base from among the plurality of skin care product bases into the container; and
after said operating the one or more of the plurality of premix dispensers and said operating the product base dispenser, mixing the contents of the container.

2. The method of claim 1, wherein a total time for completing said operating the one or more of the plurality of premix dispensers, said operating the product base dispenser, and said mixing is less than five minutes.

3. The method of claim 1, further comprising:
after said operating the one or more of the plurality of premix dispensers and said operating the product base dispenser, closing the container prior to said mixing.

4. The method of claim 1, wherein the plurality of skin care product bases includes one of:
a first skin care product base is adapted for treatment of a type of skin selected from the group consisting of oily skin, dry skin, and combined oily and dry skin; and
a second skin care product base is adapted for treatment of a different type of skin than the first skin care product base selected from the group consisting of oily skin, dry skin, and combined oily dry skin.

5. The method of claim 1, wherein the one or more of the plurality of active ingredient premixes includes two or more items selected from the group consisting of:
*Glycyrrhiza glabra* extract;
*Bellis perennis* flower extract;
kojic acid;
hydroquinone;
resveratrol;
a peptide having an International Nomenclature of Cosmetic Ingredients (INCI) name Acetyl Glycyl Beta-Alanine;
arbutin; and
L-ascorbic acid.

6. The method of claim 1, further comprising:
receiving data indicative of a customer's skin type;
wherein said generating the recipe includes selecting a skin care product base from among the plurality of skin care product bases based on the data indicative of the customer's skin type.

7. The method of claim 1, wherein the one or more of the plurality of active ingredient premixes includes:
*Glycyrrhiza glabra* extract;
*Bellis perennis* flower extract;
kojic acid and/or hydroquinone;
resveratrol;
a peptide having an International Nomenclature of Cosmetic Ingredients (INCI) name Acetyl Glycyl Beta-Alanine;
arbutin; and
L-ascorbic acid.

8. The method of claim 1, wherein the one or more of the plurality of active ingredient premixes includes two or more items selected from the group consisting of:
niacinamide;
salicylic acid;
glycolic acid;
lactic acid;
argan oil or apricot kernel oil;
a sediment having an International Nomenclature of Cosmetic Ingredients (INCI) name Silt;
charcoal; and
*Aloe barbadensis* concentrate.

9. The method of claim 1, wherein the one or more of the plurality of active ingredient premixes includes:
niacinamide;
salicylic acid;
glycolic acid;
argan oil or apricot kernel oil;
a sediment having an International Nomenclature of Cosmetic Ingredients (INCI) name Silt;
charcoal; and
*Aloe barbadensis* concentrate.

10. The method of claim 1, wherein the one or more of the plurality of active ingredient premixes includes two or more items selected from the group consisting of:
a flavonoid complex including purified water having an International Nomenclature of Cosmetic Ingredients (INCI) name Water (Aqua), butylene glycol, *Ginkgo biloba* leaf extract, phenoxyethanol, and ethylhexylglycerin;
green tea extract;
vitamin E;
dimethylaminoethanol (DMAE);
Coenzyme $Q_{10}$;
plant stem cell; and
L-ascorbyl palmitate.

11. The method of claim 1, wherein the one or more of the plurality of active ingredient premixes includes:
a flavonoid complex including purified water having an International Nomenclature of Cosmetic Ingredients (INCI) name Water (Aqua), butylene glycol, *Ginkgo biloba* leaf extract, phenoxyethanol, and ethylhexylglycerin;
green tea extract;
vitamin E;
dimethylaminoethanol (DMAE);
Coenzyme $Q_{10}$;
plant stem cell; and
L-ascorbyl palmitate.

12. The method of claim 1, wherein the one or more of the plurality of active ingredient premixes includes two or more items selected from the group consisting of:
a complex of vegetable glycerin having an International Nomenclature of Cosmetic Ingredients (INCI) name Glycerin, purified water having the INCI name Water (Aqua), a chemical having the INCI name Methylglucoside Phosphate, and a chemical having the INCI name Copper Lysinate/Prolinate;
a complex having the INCI name *Lactococcus* Ferment Lysate;
acetyl hexapeptide-3;
palmitoyl tripeptide;
algae extract;
dipalmitoyl hydroxyproline;
Vitamin E Tocopherol;
retinol;
retinyl palmitate;
hyaluronic acid; and
a chemical having the INCI name Propanediol (and) *Orobanche rapum* Extract.

13. The method of claim 1, wherein the one or more of the plurality of active ingredient premixes includes:
a complex of vegetable glycerin having an International Nomenclature of Cosmetic Ingredients (INCI) name Glycerin, purified water having the INCI name Water (Aqua), a chemical having the INCI name Methylglucoside Phosphate, and a chemical having the INCI name Copper Lysinate/Prolinate;

a complex having the INCI name *Lactococcus* Ferment Lysate;
acetyl hexapeptide-3;
palmitoyl tripeptide, algae extract, dipalmitoyl hydroxyproline and/or Vitamin E Tocopherol;
retinol and/or retinyl palmitate;
hyaluronic acid; and
a chemical having the INCI name Propanediol (and) *Orobanche rapum* Extract.

14. The method of claim 1, wherein the one or more of the plurality of active ingredient premixes includes two or more items selected from the group consisting of:
glycyrrhetinic acid, tromethamine and/or *Usnea barbata* extract;
*Chamomilla recutita* extract; and
*Glycyrrhiza glabra* extract.

15. The method of claim 1, wherein the one or more of the plurality of active ingredient premixes includes:
glycyrrhetinic acid, tromethamine and/or *Usnea barbata* extract;
*Chamomilla recutita* extract; and
*Glycyrrhiza glabra* extract.

16. The method of claim 1, wherein each of the plurality of skin care product bases do not include any active ingredients.

17. The method of claim 1, wherein receiving data indicative of a customer's skin condition comprises receiving the data from a questionnaire filled out by a customer.

\* \* \* \* \*